US00PP17031P2

(12) United States Plant Patent
Olesen

(10) Patent No.: US PP17,031 P2
(45) Date of Patent: Aug. 22, 2006

(54) COMPACT FLORIBUNDA ROSE PLANT NAME 'POULPAL024'

(50) Latin Name: ***Rosa* hybrid**
Varietal Denomination: Poulpal024

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/131,735

(22) Filed: May 17, 2005

(51) Int. Cl.
*A01H 5/00* (2006.01)

(52) U.S. Cl. ..... Plt./146

(58) Field of Classification Search ..... Plt./141, Plt./146, 147, 150

See application file for complete search history.

*Primary Examiner*—Kent Bell
*Assistant Examiner*—June Hwu

(57) ABSTRACT

A new compact floribunda rose plant that has abundant, orange red flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical classification: *Rosa* hybrid.
Variety denomination: 'Poulpal024'.

SUMMARY OF THE INVENTION

The present invention constitutes a new and distinct variety of compact floribunda rose plant which originated from a controlled crossing between the female seed parent, an un-named seedling, and the male pollen parent, a rose by the same inventors named 'Poulmanti' described and illustrated in U.S. Plant Pat. No. 11,540, issued Oct. 3, 2000. The two parents were crossed and the resulting seeds were planted in a controlled environment. The new variety is named 'Poulpal024'.

The new rose may be distinguished from the seed parent by the following combination of characteristics:

1. 'Poulpal024' has 55 to 60 petals, while the female parent has about 40 petals.
2. 'Poulpal024' has orange red flowers, while the female parent has light pink flowers.
3. 'Poulpal024' has a flower bloom diameter of 60 to 65 mm, while the female parent has a flower bloom diameter of 35 to 40 mm.

The new variety may be distinguished from its pollen parent, 'Poulmanti' by the following combination of characteristics:

1. Petal count of 'Poulpal024' is 55 to 60 petals. 'Poulmanti' has approximately 40 to 50 petals.
2. 'Poulpal024' has orange red flowers while 'Poulmanti' pink flowers.

The objective of the hybridization of this rose variety for commercial culture was to create a new and distinct variety with unique qualities, such as:

1. Uniform and abundant orange red flowers;
2. Vigorous and compact growth when propagated on it's own roots as well as from grafting;
3. Suitable variety for production in 19 cm pots;
4. Superior disease resistance;
4. Attractive, dark, glossy foliage.

This combination of qualities is not present in previously available commercial cultivars of this type, known to the inventor, and distinguish 'Poulpal024' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpal024' was selected by the inventor as a single plant from the progeny of the hybridization in June 1998.

Asexual reproduction of 'Poulpal024' by cuttings and traditional budding was first done by Mogens N. Olesen in the nursery in Fredensborg, Denmark in April 1998. This initial and other subsequent propagations conducted in controlled environments have demonstrated that the characteristics of 'Poulpal024' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems of 'Poulpal024'. Specifically illustrated in the drawings:

FIG. 1.1; Flower bud closed, partially open, and open;

FIG. 1.2; Open flower and flower petals detached;

FIG. 1.3; Sepals, receptacle, pedicel, and reproductive flower parts;

FIG. 1.4; Mature leaf;

FIG. 1.5; Juvenile leaf;

FIG. 1.6; Bare stem exhibiting thorns;

FIG. 2.0; Entire flowering plant cultivated in a 19 cm pot.

DETAILED DESCRIPTION OF THE VARIETY

The following is a description of 'Poulpal024', as observed in its growth in in Fredensborg, Denmark. Observed plants are 16 months of age and were cultivated on their own roots in 25 cm pots. Color references are made using The Royal Horticultural Society (London, England) Colour Chart, 2001, except where common terms of color are used.

For a comparison, several physical characteristics of the rose variety 'Poulac006' a rose variety from the same inventor described and illustrated in U.S. Plant patent application Ser. No. 10/342,702 dated Jan. 14, 2003, are compared to 'Poulpal024' in Chart 1.

CHART 1

| | 'Poulpal024' | 'Poulac006' |
|---|---|---|
| Petalage. | Very Double; 55 to 60 petals | 35 to 40 petals |
| General tonality of flower color | Red Group 41A. | Red Group 40A |
| Flower diameter. | 60 to 65 mm | 60 to 80 mm |

FLOWER AND FLOWER BUD

Blooming habit: Continuous.

Flower bud:

*Size.*—Upon opening, 25 mm in length from base of receptacle to the apex. 14 mm in diameter on average.

*Bud form.*—Urceolate with pointed apex.

*Bud color.*—As sepals unfold, petals are Red Group 42B to Greyed-Red Group 179A with intonations of Yellow-Green Group 145D. At ¼ opening petals become Red Group 41B with intonations of Red Group 43C.

*Sepals.*—Upper Surface: Color: Yellow-Green Group 146B and 146C. Anthocyanic intonations of Greyed-Orange 177B. Surface: Medium pubescence observed. Lower Surface: Color: Yellow-Green Group 144A. Anthocyanic pigments the color of Greyed-Purple 183A observed. Texture: Smooth with few stipitate glands. Shape: Subulate. Base is flat at the union with receptacle. Apex is cirrhose. Margins: Margins have weak foliaceous appendages. Size: 25 mm (l) by 8 mm (w) on average.

*Receptacle.*—Surface Texture: Smooth. Shape: Urn-shaped. Size: 10 mm (h)×9 mm (w) on average. Color: Yellow-Green Group 144A. Anthocyanin: Greyed-Purple Group 183A.

*Pedicel.*—Surface: Somewhat rough with stipitate glands. Length: 55 to 65 mm average. Diameter: Normally 3 mm. Color: Yellow-Green Group 144A. Strong anthocyanic pigments the color of Greyed-Purple 183B observed. Strength: Strong.

*Borne.*—1 to 3 flower buds per flowering stem observed.

Flower bloom:

*Fragrance.*—Very light floral scent.

*Duration.*—As a pot plant, flowers last 14 to 21 days. After flowers have matured petals do not fall cleanly away from plant.

*Size.*—Average flower diameter is 60 to 65 mm when open. Depth is 25 to 30 mm.

*Form.*—Rosette with many overlapping petals packed into quarter sections.

*Flower shape.*—When viewed from the side: Upon opening, upper part: Flat. Upon opening, lower part: Flattened convex. Open flower, upper part: Flattened convex. Open flower, lower part: Concave.

*Petalage.*—55 to 60 petals under normal conditions, 8 of which are petaloids.

Flower color:

*Upon opening, petals.*—Outermost petals: Upper Surface: Red Group 41A with occasional light streaks of Red Group 43D to 48D that radiate outward from the basal zone. Lower Surface: Red Group 43C with occasional streaks of Red Group 48D emanating from the petal spot and bisecting petal. Innermost petals: Upper Surface: Red Group 41A with occasional light streaks of Red Group 43D to 48D that radiate from the basal zone. Lower Surface: Red Group 43C with occasional streaks of Red Group 48D emanating from the basal zone and bisecting petal.

*Upon opening, basal petal spots.*—Upper Surface: Yellow Group 4A to 4B. Lower Surface: Yellow Group 4A to 4B.

*After opening, petals.*—Outermost petals: Upper Surface: Red Group 41A with occasional light streaks of Red Group 43D to 48D that radiate from the basal zone. Lower Surface: Red Group 43C with occasional streaks of Red Group 48D emanating from the basal zone and bisecting petal. Innermost petals: Upper Surface: Red Group 41A with occasional light streaks of Red Group 43D to 48D that radiate from the basal zone. Lower Surface: Red Group 43C with occasional streaks of Red Group 48D emanating from the basal zone and bisecting petal.

*After opening, basal petal spots.*—Outermost petals: Upper Surface: Yellow Group 4A to 4B. Lower Surface: Yellow Group 4A to 4B.

General tonality: On open flower Red Group 41A. No change in the general tonality at the end of the $10^{th}$ day.

Petals:

*Petal reflex.*—Variable. Occasionally flat and slightly reflexed.

*Petal margin.*—Entire and uniform.

*Shape.*—Broad elliptical. Base shape is accute to slightly rounded. Apex is rounded.

*Average size.*—Inner petals: 27 mm (l)×22 mm (w). Outer petals: 30 mm (l)×32 mm (w).

*Texture.*—Smooth.

*Thickness.*—Average.

*Arrangement.*—Not formal.

Petaloids:

*Size.*—Normally 20 mm (l)×5 mm (w).

*Shape.*—Elliptical and irregular with very acute base shape.

*Color.*—Upper Surface is Red Group 41A with occasional light streaks of Red Group 43D to 48D that radiate from the petal spot. Lower Surface is Red Group 43C with occasional streaks of Red Group 48D emanating from the petal spot and bisecting petal.

Reproductive organs:

*Pollen.*—Quantity: Above average. Color: Orange Group 26A.

*Anthers.*—Size: 2 mm long. Color: Yellow-Orange Group 16A with Yellow-Orange Group 17A toward margins of the anther. Quantity: Normally 100 to 110.

*Filaments.*—Color: At the base Yellow Group 9A with Yellow-Orange Group 16A toward the anthers. Length: 6 to 8 mm.

*Pistils.*—Length: 3 to 4 mm. Quantity: Average of 50 to 60.

*Stigmas.*—Inferior relative to the length of the filaments and the height of the anthers. Color: Yellow-Green Group 145D to Yellow Group 2D.

*Styles.*—Color: Yellow-Green Group 145D to Yellow Group 2D.

*Seed formation.*—Not observed.

PLANT

Plant growth: Upright to bushy. When grown as a 19 cm pot plant on its own roots, the average height of the plant itself is 35 to 45 cm and the average width is 35 to 45 cm.

Stems:

*Color.*—Young wood: Older wood: Yellow-Green Group 146B.

*Diameter.*—5 mm.

*Internodal distance.*—45 mm.

*Length of stems.*—On average canes are 25 cm from the base of the stem to the flowering portion.

*Surface texture.*—Young wood: Smooth. Older wood: Smooth.

Thorns:

*Incidence.*—Normally 11 thorns per 10 cm of stem.

*Color.*—Greyed-Red Group 182A to 182B with intonations of Greyed-Yellow 162B.

*Shape.*—Upper side: Concave. Lower side: Concave.

Plant foliage: Normal number of leaflets on normal leaves in middle of the stem: 7 leaflets.

*Compound leaf size.*—150 mm (l)×90 mm (w).

*Quantity.*—2 leaves per 10 cm of stem.

*Color.*—Mature foliage: Upper Leaf Surface: Yellow-Green Group 147A. Lower Leaf Surface: Yellow-Green Group 146B.

Plant leaves and leaflets:

*Stipules.*—Size: 20 mm. Shape: Linear, slightly broad based with outward extending apecies. Margins: Entire, and finely serrated. Color: Yellow Green Group 144A.

*Petiole.*—Length: 25 mm. Diameter: 2 mm. Color: Upper surface is Yellow-Green Group 146B. Lower surface is Yellow-Green Group 144A. Anthocyanin the color of Greyed-Purple Group 183A observed at the point of leaflet attachment. Underneath: Few small prickles on lower section observed. Few stipitate glands on upper section observed.

*Rachis.*—Size: 65 to 70 mm. Color: Upper surface is Yellow-Green Group 146B. Anthocyanin at point of leaflet attachment is Greyed-Purple 183A. Lower surface Yellow-Green Group 145B. Underneath: Few small thorns observed on underside. Few stipitate glands on upper portion observed.

*Leaflet.*—Size: The terminal leaflet is normally 50 mm (l)×40 mm (w). Edge: Serrated. General Shape: Elliptical to orbicular. Apex Shape: Cuspidate. Base Shape: Rounded. Texture: Smooth. Thickness: Average. Arrangement: Odd pinnate. Venation: Reticulate. Leaf Gloss: Glossy finish.

Disease resistance: Above average resistance to powdery and downy mildew, black spot, and *Botrytis* under normal growing conditions in Fredensborg, Denmark.

It is claimed:

1. A new and distinct variety of rose plant of the compact floribunda class named 'Poulpal024', illustrated and described herein, due to its abundant, orange red flowers, vigorous growth, compact habit, suitability for production from softwood cuttings in pots, and durable flowers and foliage that make the variety suitable for distribution in the floral industry.

* * * * *

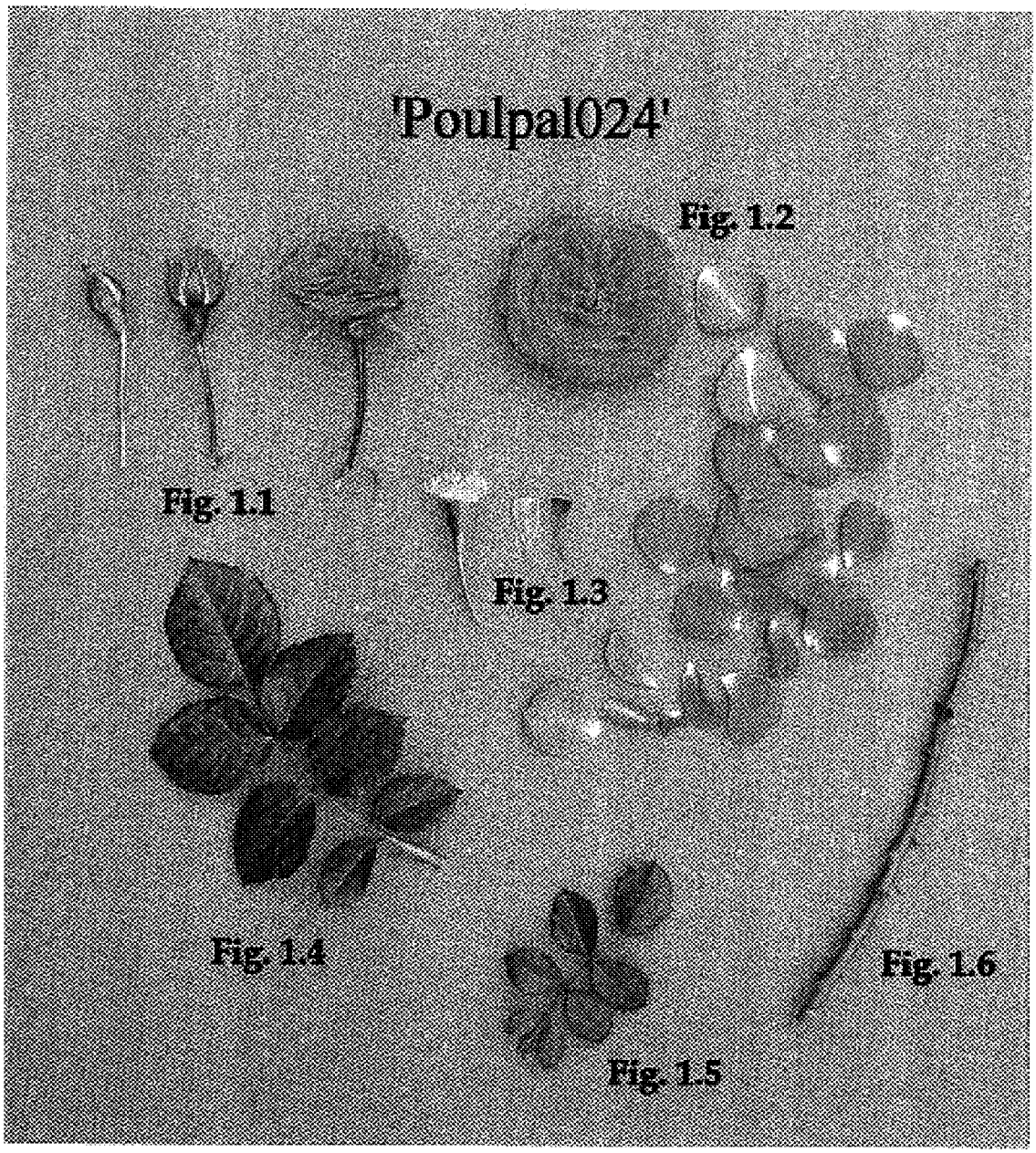
'Poulpal024'
Fig. 1.1
Fig. 1.2
Fig. 1.3
Fig. 1.4
Fig. 1.5
Fig. 1.6

'Poulpal024'
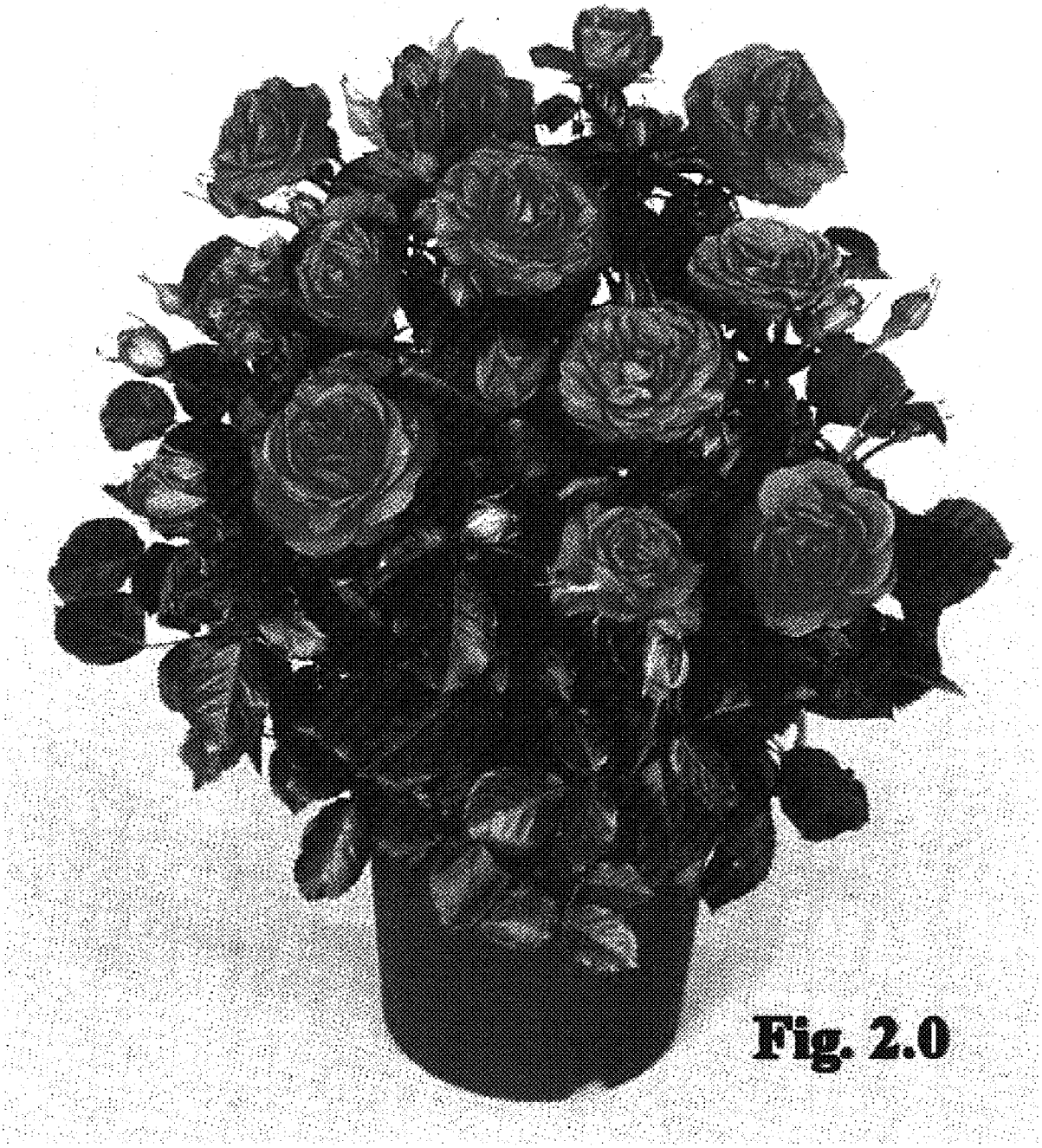
Fig. 2.0